US00PP21347P2

(12) United States Plant Patent
Deng et al.

(10) Patent No.: US PP21,347 P2
(45) Date of Patent: Sep. 28, 2010

(54) ***CALADIUM* PLANT NAMED 'UF340'**

(50) Latin Name: *Caladium×hortulanum*
Varietal Denomination: UF340

(75) Inventors: Zhanao Deng, Ellenton, FL (US); Brent Harbaugh, Bradenton, FL (US)

(73) Assignee: Florida Foundation Seed Producers, Inc., Greenwood, FL (US)

( * ) Notice: Subject to any disclaimer, the term of this patent is extended or adjusted under 35 U.S.C. 154(b) by 0 days.

(21) Appl. No.: 12/383,382

(22) Filed: Mar. 24, 2009

(51) Int. Cl.
*A01H 5/00* (2006.01)

(52) U.S. Cl. ..... Plt./373

(58) Field of Classification Search ..... Plt./373
See application file for complete search history.

*Primary Examiner*—Susan B McCormick Ewoldt

(57) ABSTRACT

A new *Caladium* plant named 'UF340' particularly distinguished by its large number of wide lance leaves having a large, bright, and pure white center surrounded by green margins, and demonstrated potential to produce attractive plants in outdoor landscapes, and produce attractive pot plants when tubers are forced in containers, is disclosed.

1 Drawing Sheet

ACKNOWLEDGEMENT OF FEDERAL RESEARCH SUPPORT

Figure 1:
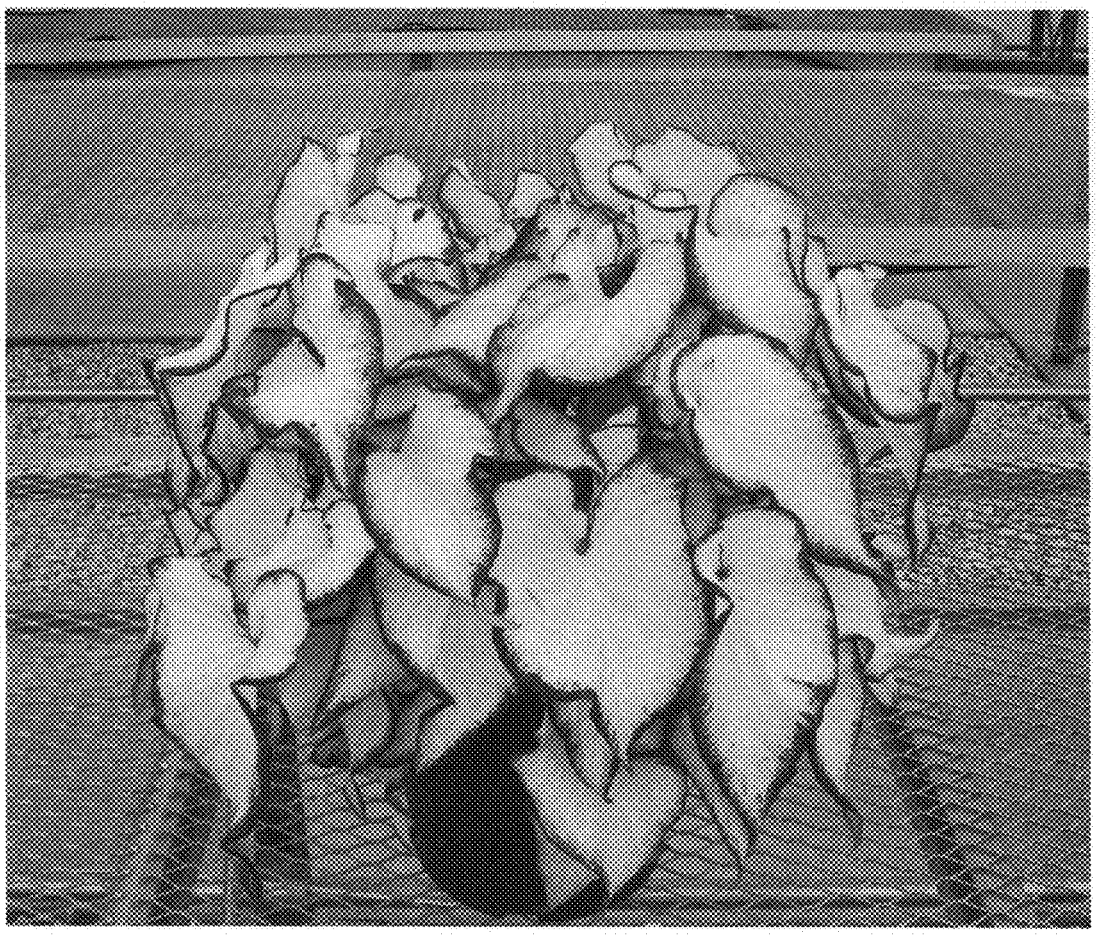

This invention was made with government support under FLA-BRA-04162 awarded by the Cooperative State Research, Education, and Extension Service, USDA. The government has certain rights in this invention.

Genus and species: *Caladium×hortulanum.*

Variety denomination: 'UF340'.

BACKGROUND OF THE NEW PLANT

The invention relates to a new and distinct variety of *Caladium×hortulanum* plant named 'UF340'. 'UF340' originated from a controlled pollination made in the spring of 2003 between 'Florida Sweetheart' (U.S. Plant Pat. No. 8,526) and 'Florida Moonlight' (U.S. Plant Pat. No. 14,565). 'Florida Sweetheart', the pollen parent, is a progeny of the cross between 'Candidum Junior' (unpatented) and 'Red Frill' (unpatented). The ancestry of 'Candidum Junior' and 'Red Frill' is unknown, although 'Candidum Junior' was suspected to be a field mutation of 'Candidum' (unpatented). 'Florida Moonlight', the seed parent, is a progeny of the cross between 'Aaron' (unpatented) and 'Candidum Junior'. 'UF340' was initially selected in 2003 as GCREC-3230. Asexual propagation of tubers and evaluation in field and pot studies in Wimauma, Fla. since 2004 have shown that the unique features of 'UF340' are stable and reproduced true to type in successive generations of asexual propagation.

Plant Breeder's Rights for this cultivar have not been applied for. 'UF340' has not been made publicly available more than one year prior to the filing of this application.

SUMMARY OF THE INVENTION

*Caladium* [*Caladium×hortulanum* Birdsey, Araceae Juss.] is commonly used as a pot or landscape plant and is valued for its colorful leaves. Commercial *caladium* plants are grown from tubers. The commercial value of a *caladium* cultivar depends on its tuber yield, leaf color, performance in the landscape as a garden plant, and performance in containers as a pot plant.

The new and distinct variety of *caladium* is a white lanced-leaved *caladium* that possesses a novel combination of foliar characteristics. 'UF340' is distinct from other lance-leaved varieties in that it developed a large number of wide lance leaves with a large, bright, and pure white center surrounded by green margins. 'UF340' has improved performance in container forcing and landscape planting compared to other commercial white lance-leaved varieties. When forced in containers, 'UF340' sprouts 5-10 days earlier than other commercial white lance-leaved varieties.

DESCRIPTION OF THE PHOTOGRAPHS

This new *caladium* plant is illustrated by the accompanying photograph which shows the plant's form and foliage. The new *caladium* has not been observed under all possible environmental conditions. Its phenotype may vary somewhat with variations in the environment such as light intensity and temperature, without, however, any variance in genotype. The colors shown are as true as can be reasonably obtained by conventional photographic procedures. Colors in the photograph may differ slightly from the color values cited in the detailed botanical description, which accurately describe the colors of the new *Caladium.*

FIG. 1 shows the overall plant appearance and habit including foliage from a side perspective view of a typical plant of the new *Caladium* grown in a container.

DESCRIPTION OF THE NEW CULTIVAR

The following detailed description sets forth the distinctive characteristics of 'UF340' with color terminology in accordance with British Color Council and The Royal Horticultural Society, Horticultural Colour Chart, except where general color terms of ordinary dictionary significance are obvious. Wherein dimensions, sizes, and other characteristics are given, it is to be understood that such characteristics are approximations of averages set forth as accurately as practicable. The description herein is from 4 month-old specimens grown in Wimauma, Fla., in 2007. Plants used for describing color were grown in 20.3-cm containers in a 45% shaded greenhouse from four No. 1 (3.8 to 6.4 cm in diameter) tubers.

DETAILED BOTANICAL DESCRIPTION

Classification:

*Botanical.*—*Caladium×hortulanum.*

*Common name.*—*Caladium.*

Parentage:

*Female parent.*—'Florida Moonlight' (U.S. Plant Pat. No. 14,565) *caladium.*

*Male parent.*—'Florida Sweetheart' (U.S. Plant Pat. No.8.526) *caladium.*

Propagation:

*Type.*—By tuber division.

*Time to develop roots and sprout.*—26 days (Spring — 15° C. night to 29° C. day). 14 days (Summer — 21° C. night to 35° C. day).

*Root description.*—Dense, moderately thick roots (up to 2.5 mm at the basal end) with little branching and few lateral roots.

Plant description:

*Plant shape.*—Mounding, symmetrical.

*Plant height.*—About 27 cm from top of soil to top of leaf plane 4 months from planting tubers in ground beds in full sun.

*Plant width.*—About 25-40 cm 4 months from planting tubers in ground beds in full sun.

*Leaf blade.*—Saggittate-cordate, 15-21 cm long and 10-15 cm wide, and slightly undalate with a white (RHS 155D) penniform venation. Two lobes are up to one third of the leaf length. The upper surface has a green (RHS 138A) margin, up to 10 mm wide, bordering the entire leaf except for the basal leaf valley formed by the two lobes where it is greyed-purple (RHS 185B). The central and main veins are white (RHS 155C). Interveinal areas are white (RHS 155B) except for the areas near the margin, where irregular light green (RHS 136C) mottling is present. A 1-2 mm greyed-purple line (RHS 185B) is present on the basal leaf collar at the petiole apex. The undersurface has a greyed-green (RHS 191A) margin, up to 10 mm wide, and a white (RHS 155D) center and light green (RHS 130D) central and main veins. Secondary veins are light green (RHS 130D) and netted. The largest leaf on plants grown in a 45% shaded greenhouse produced from an intact No. 1 tuber in an 11.4-cm pot averaged 19 cm long and 13 cm wide 8 weeks after planting. When grown from 2.54-cm tuber propagules in ground beds with full sun, leaves measured approximately 4 months from planting averaged 18 cm long and 13 cm wide.

*Petiole.*—Aspect: Mostly erect, curving outwardly with development. Length: 19.5 -24.5 cm. Diameter (distal): 4 mm. Diameter (proximal): 5.5 mm. Strength: Medium, soft. Color (distal): White (RHS 155D) to yellow-green (RHS 145B). Color (proximal): Black (RHS 202A) with streaks and blotches of orange-white (RHS 159B). Wing length: 3-5 cm. Wing diameter: 4-5.5 mm. Wing color: Black (RHS 202A) with blotches of orange-white (RHS 159C).

*Tuber.*—Jumbo-sized (6.4 to 8.9 cm in diameter) tubers are multi-segmented, bearing 5 to 9 dominant buds. Tuber surfaces are brown (RHS 200C) with the cortical area yellow-orange (RHS 10C).

*Inflorescence.*—The inflorescences of 'UF340' have been observed only on shadehouse-grown plants. Inflorescence arrangement: Upright hooded spathes surrounding a columnar spadix borne on a tall upright scape. Fragrance: None detected. Natural flowering season/longevity: Plants of 'UF340' typically flower during the spring or early summer in central Florida. Flowers develop about seven weeks after growth commences. Inflorescences last about three days before fading; inflorescences persistent. Spathe: Length: 9 cm. Width, distal: 1.5 cm. Width, proximal: 1 cm. Shape: Ovate to somewhat obovate. Apex: Acute to acuminate. Base: Tapering. Margin: Entire; proximal, notched. Texture (upper and lower surfaces): Smooth, glabrous. Spadix: Spadix with sessile, simple female and male flowers separated into two zones. Female flowers arranged on the lower one-third of the spadix; male flowers arranged on the upper two-thirds of the spadix. Sterile flowers develop between female and male flower zones. Near this area, the spathe constricts surrounding the female flowers. Length (entire spadex): 4.5 cm. Length (male flower zone): 2.5 cm. Length (sterile flower zone): 1 cm. Length (female flower zone): 1 cm. Diameter (male flower zone): 4.5 mm. Diameter (sterile flower zone): 2.5 mm. Diameter (female flower zone): 4.5 mm. Shape: Spindle-shaped to columnar. Apex: Obtuse. Base: Obtuse. Aspect: Upright. Color (mature, male zone): yellow-white (RHS 158B). Color (mature, sterile zone): yellow-white (RHS 158B). Color (mature, female zone): yellow (RHS 11C). Male flowers: Quantity per spadix: About 200. Shape: Obovate. Height: 2.5 mm. Diameter: 2 mm. Anther color: RHS 157D. Amount of pollen: Moderate. Female flowers: Quantity per spadix: About 60. Shape: Obovate. Height: 3 mm. Diameter: 2 mm. Stigma color: RHS 9C. Ovary color: RHS 155D. Scape: Length: 11 cm. Strength: Sturdy, flexible. Aspect: Erect. Texture: Smooth, glabrous. Seed and Fruit: No fruit or seed without hand pollination.

COMPARISON WITH KNOWN CULTIVARS

Plants of 'UF340' differ from plants of the female parent, 'Florida Moonlight' (U.S. Plant Pat. No. 14,565), in the following characteristics:

1. Plants of 'UF340' are shorter than plants of the female parent;
2. Plants of 'UF340' differ from the female parent in leaf shape as plants of the female parent have fancy (or heart) shaped leaves;
3. Leaves of 'UF340' are much smaller than leaves of the female parent.

Plants of 'UF340' differ from plants of the male parent, 'Florida Sweetheart' (U.S. Plant Pat. No. 8,526) in the following characteristics:

1. Plants of 'UF340' and 'Florida Sweetheart' differ in leaf coloration, as leaves of 'Florida Sweetheart' have light pink color in the center and pink veins.

Additionally, comparisons were made with the commercial varieties 'Florida White Ruffles' (U.S. Plant Pat. No.

14,402) and 'White Wing' (unpatented). Comparisons were made in Wimauma, Fla. in 2006 and 2007.

Field plots were organized in a randomized complete block design consisting of three replications, and each plot contained 30 propagules. Tubers were dug in Dec. 2006 and Jan. 2008, respectively. Dried tubers were graded by maximum diameter; No. 2 (2.5 to 3.8 cm), No. 1 (3.8 to 6.4 cm), Jumbo (6.4 to 8.9 cm), Mammoth (8.9 to 11.4 cm), and Super Mammoth (>11.4 cm). The production index, an indicator of economic value of the harvested tubers, was calculated as: N (No. 2) + 2N (No. 1) + 4N (Jumbo) + 6N (Mammoth) + 8N (Super Mammoth); where N=number of tubers in each grade. The average tuber weight of 'UF340' was lower than that of 'White Wing' and 'Florida White Ruffles' in 2006 (Table 1), but in 2007, the average tuber weight of 'UF340' was approximately 3.5x that of 'White Wing' and 'Florida White Ruffles'. The production index of 'UF340' was similar to that of 'Florida White Ruffles' and 'White Wing' in 2006, and in 2007, 'UF340' was approximately 2.7x greater than that of 'White Wing' and 'Florida White Ruffles'. In both 2006 and 2007, 'UF340' consistently produced the greatest number of marketable tubers, significantly higher than both 'White Wing' and 'Florida White Ruffles'. The majority of the tubers produced by 'UF340' were in the No. 1, No. 2 and Jumbo categories, with few in the mammoth size category.

Landscape performance of the varieties grown under full-sun conditions was evaluated in 2006 and 2007 on the same plots used for evaluating tuber production. The overall plant performance was rated multiple times (July, August, and September) in each growing season, on a scale of 1 to 5, with 1 being very poor (few leaves and lack of vigor), and 5 being excellent (full plants, numerous leaves, and bright color display). Similarly, leaf sun burn tolerance was also evaluated multiple times in each growing season on a scale of 1 to 5, with 1 being very susceptible to sun burns and showing numerous sun-damaged areas or holes on leaves and 5 being resistant to sun bums and not showing any sun-damaged areas. At approximately 4 months after planting, plant height, number of leaves, and foliar characteristics were measured. 'UF340' was 27 cm tall, which was similar to 'White Wing' (24 cm), but was taller than 'Florida White Ruffles' (18 cm), a very prostrate variety (Table 2). 'UF340' produced the greatest number (33) of leaves, exceeding both 'Florida White Ruffles' (27) and 'White Wing' (20). Leaves of 'UF340' were similar to those of 'White Wing' in length, but longer than those of 'Florida White Ruffles', and wider than both varieties. The performance ratings of 'UF340'were 3.9 to 4.4, which was higher than that of 'Florida White Ruffles' and 'White Wing'.

The varieties' suitability for container forcing was evaluated by forcing tubers in 11.4-cm containers. No. 1 tubers were planted either intact or de-eyed in a peat/vermiculite mix on Mar. 26, 2007. The study was conducted in a greenhouse with 45% light exclusion during the summer in Wimauma, Fla. Average daily temperatures ranged from a low of 16° C. night to 29° C. day during the experiment. Potted plants were arranged on metal benches in the greenhouse in a randomized complete block design with 10 replications. Plant height, number of leaves, and foliar characteristics were recorded 8 to 10 weeks after planting. 'UF340' sprouted 26 (intact) to 28 (de-eyed) days after planting, significantly earlier (5 to 10 days) than both 'White Wing' and 'Florida White Ruffles', regardless of tuber treatments (Table 3). 'UF340' was similar to 'Florida White Ruffles' and 'White Wing' in height whether tubers were intact or de-eyed. 'UF340' produced more leaves, especially when tubers were de-eyed, than 'Florida White Ruffles' and 'White Wing'. 'UF340' produced high quality plants in small pots (11.4 cm in diameter) even without de-eyeing (Table 3). When tubers were de-eyed, 'UF340' yielded pot plants of even higher quality with a plant quality ratings greater than those of 'White Wing' and 'Florida White Ruffles'.

TABLE 1

Tuber weight, production index, number, and tuber grade distribution of 'UF340' and two commercial cultivars harvested in 2006 and 2007. Values presented are means of three replications with 30 propagules planted in a plot per year.

| | Tuber | | | Tuber distribution[x] (%) | | | | |
|---|---|---|---|---|---|---|---|---|
| Varieties | Weight (kg) | Production index[y] | Marketable (no.) | Super mammoth | Mammoth | Jumbo | No. 1 | No. 2 |
| | Year 2006 | | | | | | | |
| UF340 | 3.8 | 157 | 70 | 0 | 5 | 18 | 50 | 27 |
| Florida White Ruffles | 4.4 | 163 | 55 | 1 | 17 | 26 | 30 | 27 |
| White Wing | 5.7 | 164 | 50 | 3 | 13 | 38 | 33 | 13 |
| | Year 2007 | | | | | | | |
| UF340 | 3.5 | 155 | 66 | 2 | 6 | 21 | 28 | 43 |
| Florida White Ruffles | 1.0 | 43 | 30 | 0 | 1 | 4 | 27 | 68 |
| White Wing | 0.9 | 41 | 29 | 0 | 0 | 4 | 33 | 63 |

[x]Tubers graded by maximum diameter; No. 2 (2.5 to 3.8 cm), No. 1 (3.8 to 6.4 cm), Jumbo (6.4 to 8.9 cm), Mammoth (8.9 to 11.4 cm), and Super Mammoth (>11.4 cm).
[y]The production index is an indicator of economic value of the crop harvested and is calculated as: N (No. 2) + 2N (No. 1) + 4N(Jumbo) + 6N (Mammoth) + 8N (Super Mammoth), where N = number of tubers in each grade.

TABLE 2

Plant characteristics, performance, and sun tolerance ratings of 'UF340' and two commercial cultivars grown from planting 2.54-cm *caladium* tuber propagules in ground beds in full sun (2006 and 2007). Values presented for plant height, leaf number, length and width are means of three replications with three plants measured per plot per year, while performance and sun burn tolerance ratings are means of three replications based on whole plot evaluation.

| Varieties | Plant ht[z] (cm) | Leaves[z] (no.) | Leaf length[z] (cm) | Leaf width[z] (cm) |
|---|---|---|---|---|
| UF340 | 27 | 33 | 18 | 13 |
| Florida White Ruffles | 18 | 27 | 16 | 8 |
| White Wing | 24 | 20 | 18 | 10 |

| Varieties | Performance ratings[y] | | | Sun tolerance rating[x] | | |
|---|---|---|---|---|---|---|
| | July | August | September | July | August | September |
| UF340 | 4.2 | 3.9 | 4.4 | 4.5 | 4.0 | 3.7 |
| Florida White Ruffles | 2.0 | 2.9 | 3.5 | 4.5 | 4.1 | 4.2 |
| White Wing | 2.0 | 2.3 | 2.9 | 4.2 | 4.1 | 4.3 |

[z]Data were taken over two growing seasons (2006 and 2007), approximately 4 months (August 2006 and 2007) after tubers were planted in April each year.
[y]Plants were rated on a scale of 1 to 5, with 1 being very poor, 3 fair and acceptable, and 5 being excellent in plant vigor, fullness, and color display, in July, August, and September in 2006 and 2007, respectively.
[x]Plants' sun burn tolerance was rated on a scale of 1 to 5, with 1 being very poor, 3 fair and acceptable, and 5 being excellent without showing any signs of leaf burns or resulted holes on leaf surfaces, taken in July, August, and September in 2006 and 2007, respectively.

TABLE 3

Plant performance for *caladium* cultivars grown from No. 1 tubers in 11.4-cm containers in a 45% shaded glasshouse, 2007, Wimauma, Fla.
Values represent the means of 10 plants produced from intact or de-eyed No. 1 (>3.8 and <6.4 cm in diameter) tubers planted individually per container. Data was taken 8 weeks after planting.

| | Days to sprout[z] | | Plant height (cm) | | Leaves (no.) | |
|---|---|---|---|---|---|---|
| Varieties | Intact | De-eye | Intact | De-eye | Intact | De-eye |
| UF340 | 26 | 28 | 19 | 19 | 13 | 20 |
| Florida White Ruffles | 36 | 36 | 18 | 17 | 11 | 13 |
| White Wing | 31 | 35 | 19 | 18 | 8 | 11 |

TABLE 3-continued

Plant performance for *caladium* cultivars grown from No. 1 tubers in 11.4-cm containers in a 45% shaded glasshouse, 2007, Wimauma, Fla.
Values represent the means of 10 plants produced from intact or de-eyed No. 1 (>3.8 and <6.4 cm in diameter) tubers planted individually per container. Data was taken 8 weeks after planting.

| | Leaf length (cm) | | Leaf width (cm) | | Quality rating | |
|---|---|---|---|---|---|---|
| Varieties | Intact | De-eye | Intact | De-eye | Intact | De-eye |
| UF340 | 19 | 19 | 13 | 13 | 4.0 | 4.6 |
| Florida White Ruffles | 20 | 20 | 11 | 11 | 3.3 | 3.5 |
| White Wing | 19 | 18 | 12 | 9 | 3.2 | 4.0 |

[z]Number of days from planting to the first unfurled leaf.

I claim:

1. A new and distinct cultivar of *Caladium* plant as shown and described herein.

* * * * *